United States Patent [19]

McLay et al.

[11] Patent Number: 5,389,649
[45] Date of Patent: Feb. 14, 1995

[54] OXATHIANE DERIVATIVES

[75] Inventors: Iain M. McLay; Roger J. A. Walsh, both of Dagenham, United Kingdom

[73] Assignee: Rhone-Poulenc Rorer Limited, Eastbourne, England

[21] Appl. No.: 910,297

[22] PCT Filed: Jan. 17, 1991

[86] PCT No.: PCT/EP91/00075
§ 371 Date: Jul. 20, 1992
§ 102(e) Date: Jul. 20, 1992

[87] PCT Pub. No.: WO91/10659
PCT Pub. Date: Jul. 25, 1991

[30] Foreign Application Priority Data

Jan. 19, 1990 [GB] United Kingdom ............... 9001327

[51] Int. Cl.⁶ .......................................... C07D 411/04
[52] U.S. Cl. .................... 514/336; 546/268; 546/175; 546/145; 548/195; 548/469; 544/238; 544/333; 544/336; 549/14; 514/314; 514/307; 514/252; 514/256; 514/414; 514/433; 514/365
[58] Field of Search .................. 546/268; 514/336

[56] References Cited

U.S. PATENT DOCUMENTS 5,120,852 6/1992 Aloup et al. ..................... 546/268

FOREIGN PATENT DOCUMENTS 1494186 9/1967 France.
3808024 9/1988 Germany.

OTHER PUBLICATIONS

Appel, Current Neurology vol. p. 108 1987.

*Primary Examiner*—Jane T. Fan
*Attorney, Agent, or Firm*—James A. Nicholson; Martin F. Savitzky; Raymond S. Parker, III

[57] ABSTRACT

Oxathiane derivatives of formula

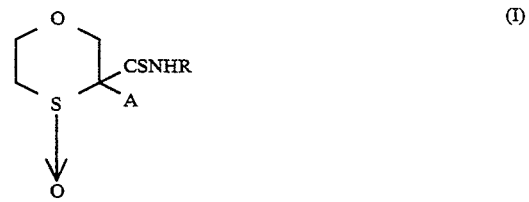

in which R represents alkyl and A represents optionally substituted phenyl or a heteroaromatic group containing 1 or 2 nitrogen atoms optionally substituted by alkyl, alkoxy or halogen, and salts thereof possess pharmacological activity and are also useful in inhibiting head hair loss.

6 Claims, No Drawings

OXATHIANE DERIVATIVES

This invention relates to new therapeutically useful oxathiane derivatives, to processes for their preparation and to pharmaceutical compositions containing them.

The new oxathiane derivatives of the present invention are those compounds of formula (I), hereinafter depicted wherein:

R represents an alkyl group; and

A represents:

(1) a phenyl or naphthyl group which is optionally substituted by one or more substituents selected from halogen atoms and cyano, nitro, trifluoromethyl, carbamoyl, carboxyl, alkoxycarbonyl, alkylsulphonyl, alkyl and phenylalkyl groups; or (2) a heteroaromatic group containing 1 or 2 nitrogen atoms, for example selected from pyrid-3-yl, quinolin-3-yl, isoquinolin-4-yl, pyridazin-4-yl, pyrimidin-5-yl, pyrazin-3-yl, indol-3-yl and thiazol-5-yl, optionally substituted by an alkyl or alkoxy group, or a halogen atom;

wherein all alkyl groups and moieties, including those in alkoxy and alkoxycarbonyl groups, are straight-chain or branched, and, unless otherwise specified, contain one to about six carbon atoms; and pharmaceutically acceptable salts thereof.

Preferred values for A include 3,4-dichlorophenyl and 3-pyridyl and R is preferably methyl.

When A represents an optionally substituted phenyl group it is preferably a phenyl group which is unsubstituted or substituted on the 3-position or on the 3- and 5-positions by substituents selected from halogen atoms and cyano, nitro, trifluoromethyl, carbamoyl, carboxyl, alkoxycarbonyl and alkylsulphonyl groups.

It is also preferred that the sulphoxide oxygen and the —CSNHR group are in the trans relationship.

In certain cases the substituents A and R can contribute to stereoisomerism. All such forms are embraced by the present invention.

Particularly important compounds of the present invention include the following:

A (±)-trans-3-(3,4-dichlorophenyl)-N-methyl-1,4-oxathiane-3-carbothioamide 4-oxide B (±)-trans-N-methyl-3-(3-pyridyl)-1,4-oxathiane-3-carbothioamide 4-oxide.

as well as their stereoisomeric forms and pharmaceutically acceptable salts thereof.

Letters A and B are allocated to compounds for ease of reference in other parts of the specification.

The compounds have valuable pharmacological properties, in particular properties which are indicative of utility in the treatment and/or prophylaxis of disorders associated with:

(1) vascular smooth muscle contraction including hypertension and other cardiovascular disorders such as congestive heart failure, and conditions associated with tissue ischaemia such as angina, peripheral vascular disease and cerebrovascular disease;

(2) respiratory smooth muscle contraction including reversible airways obstruction and asthma;

(3) contraction of smooth muscle of gastrointestinal tract, urinary bladder and uterus, including peptic ulcers, irritable bowel syndrome and diverticular disease; irritable bladder syndrome; and premature labour.

The compounds also have utility in the inhibition of head hair loss associated with male pattern baldness, by topical application.

Compounds within the scope of the present invention exhibit positive pharmacological activities as demonstrated by in vitro tests which are believed to correlate to pharmacological activity in humans and other animals.

For example, compounds of general formula (I) were submitted to:

VASO-RELAXANT ACTIVITY TEST

The test method used was adapted from those described by Winslow et al [Eur.J.Pharmacol., 131, 219-228 (1986)] and Karaki [J.Pharmacol. Methods, 18, 1-21 (1987)] for differentiating vaso-relaxant activity.

Thoracic aorta was removed from rats and transverse strips, denuded of endothelium, were suspended in a bath containing Krebs solution. The tension was recorded and a contraction induced by addition of 20 mM K+ (potassium ion) to the bathing solution. The test compound was added to the bath as a solution in increasing cumulative concentration. The concentration in the bathing solution of the test compound which reduced the K+-induced contraction by 90% was determined and expressed in $\mu M$ as the effective concentration ($EC_{90}$), given in Table 1.

TABLE 1

| Compound | $EC_{90}\ \mu M$ |
|---|---|
| A | 0.3 |
| B | 2 |

The compounds of general formula (I) can be prepared by the application and adaptation of known methods, for example as hereinafter identified. By the term "known methods" as used in this specification is meant methods heretofore used or described in the literature.

According to a feature of the present invention, the compounds of general formula (I), wherein A and R are as hereinbefore defined, are prepared by the reaction of a compound of formula (II), wherein A is as hereinbefore defined and $R^1$ is alkyl, as hereinbefore defined, or a benzyl or carboxymethyl radical, with a compound of formula:

R—NH₂            (III)

wherein R is as hereinbefore defined.

The reaction is generally carried out using an excess of amine (III), without a solvent, or in an inert organic solvent such as an ether, an aromatic hydrocarbon, an alcohol (e.g. ethanol) or dimethylsulphoxide, or a mixture of these solvents normally at room temperature, optionally under pressure and optionally in the presence of thiol acceptor, such as a heavy metal salt (e.g. mercuric chloride). The amine may be added as a solution in an alcohol (e.g. ethanol).

Compounds of formula (II), wherein A and $R^1$ are as hereinbefore defined, can be prepared by the reaction of compounds of formula (IV), wherein A is as hereinbefore defined, with carbon disulphide, followed by reaction with a compound of formula:

$R^1$—X            (V)

wherein $R^1$ is as hereinbefore defined and X is halogen, preferably iodine or a readily displaceable ester groups such as methanesulphonyloxy or 4-toluenesulphonyloxy.

The reaction is generally carried out in an anhydrous, inert, organic solvent such as dimethylformamide, at a temperature from −70° C. to room temperature, and in the presence of an organic base such as a potassium alkoxide (e.g. the tert-butoxide), or an organolithium compound, or sodium hydride.

Compounds of formula (IV), wherein A is as hereinbefore defined, can be made by oxidation of the corresponding compounds of formula (VI). This is typically by reaction with a peroxy acid (e.g. meta-chloroperbenzoic acid) in an inert solvent, such as dichloromethane, at or below room temperature.

Compounds of formula (VI), wherein A is as hereinbefore defined, can be prepared by the reaction of a compound of formula:

AMgBr     (VII)

wherein A is as hereinbefore defined (usually prepared from the corresponding bromide by conventional means), with 3-chloro-1,4-oxathiane.

This is typically carried out in an inert solvent such as benzene, at or below room temperature.

Alternatively, compounds of formula (IV) can be prepared by the reaction of compounds of formula:

A—CH$_2$—S(O)—(CH$_2$)$_2$—OH     (VIII)

wherein A is as hereinbefore defined, with formaldehyde.

This reaction is generally carried out in an inert solvent such as dimethylformamide, in the presence of an organic base, such as potassium tert-butoxide, and under ice cooling.

Compounds of formula (VIII), wherein A is as hereinbefore defined, can be prepared by the oxidation of the corresponding compounds of formula:

A—CH$_2$—S—(CH$_2$)$_2$—OH     (IX)

wherein A is as hereinbefore defined, generally under conditions similar to those described above for the conversion of compounds of formula (VI) to those of formula (IV).

Compounds of formula (IX), wherein A is as hereinbefore defined, can be prepared by the reaction of a compound of formula:

A—CH$_2$—X$^1$     (X)

or a salt thereof, wherein A is as hereinbefore defined and X$^1$ is a halogen, preferably chlorine, atom, with 2-mercaptoethanol.

This reaction is typically carried out in an inert organic solvent such as an alcohol (e.g. ethanol), in the presence of an organic base (e.g. sodium ethoxide), at temperatures up to reflux.

Compounds of formulae (III), (V), (VII) and (X) can be made by application or adaptation of known methods or are readily available.

It will be understood that it may be desirable to change one or more of the substituents on the aryl groups at an appropriate stage during the synthesis of the compounds of the invention. For example, the compounds of general formula (I) wherein A represents a phenyl group substituted by a carbamoyl group may be alternatively prepared from the corresponding compounds of general formula (I) wherein A represents a phenyl group substituted by a cyano group by the application or adaptation of known methods for such conversion.

By the term "pharmaceutically acceptable salts" as used in this specification is meant salts the anions or cations of which are relatively innocuous to the animal organism when used in therapeutic doses so that the beneficial pharmaceutical properties of the parent compounds of general formula (I) capable of forming salts are not vitiated by side-effects ascribable to those anions or cations.

It is to be understood that, where in this specification reference is made to compounds of formula (I), it is intended to refer also, where the context so permits, to their pharmaceutically acceptable salts.

Suitable acid addition salts for use in pharmaceuticals may by selected from salts derived from inorganic acids, for example hydrochlorides, hydrobromides, phosphates, sulphates and nitrates, and organic acids, for example oxalates, lactates, tartrates, acetates, salicylates, citrates, propionates, succinates, fumarates, maleates, methylene-bis-β-hydroxynaphthoates, gentisates and di-p-toluoyltartrates.

Suitable salts with bases include alkali metal (e.g. sodium and potassium), alkaline earth metal (e.g. calcium and magnesium), ammonium and amine (e.g. diethanolamine, triethanolamine, octylamine, morpholine and dioctylmethylamine) salts.

As well as being useful in themselves as active compounds, pharmaceutically acceptable salts of the compounds of general formula (I) capable of forming salts with acids or bases are useful for the purposes of purification of the parent compounds of general formula (I), for example by exploitation of the solubility differences between the salts and the parent compounds, by techniques well known to those skilled in the art.

The thioformamide derivatives of general formula (I) obtained by the aforedescribed processes can be purified by the usual physical methods, in particular crystallisation and chromatography, especially to resolve mixtures of enantiomers using a chiral column.

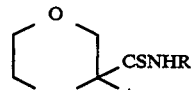 (I)

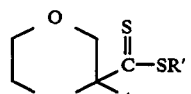 (II)

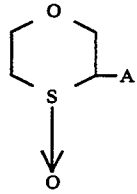 (IV)

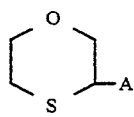

The following Examples illustrate the preparation of compounds according to the present invention.

EXAMPLE 1

Compound A

A suspension of (±)-trans-3-(3,4-dichlorophenyl)-3-methylthiothiocarbonyl-1,4-oxathiane 4-oxide (730 mg, 2 mmol) in ethanol (20 ml) and dimethylsulphoxide (2.8 ml) was treated with methylamine solution (1.5 ml, 33% in ethanol, 15.7 mmol) and the mixture stirred for 1.5 hrs at room temperature. The mixture was then evaporated in vacuo and partitioned between dichloromethane (25 ml) and water (25 ml). The organic layer was dried (MgSO$_4$) evaporated in vacuo and purified by flash chromatography on silica, eluting with ethyl acetate to give (±)-trans-3-(3,4-dichlorophenyl)-N-methyl-1,4-oxathiane-3-carbothioamide 4-oxide (220 mg), as colourless crystalline solid, m.p. 213°–214° C.;

[Found: C, 43.0; H, 4.07; Cl, 19.6% Calculated for C$_{12}$H$_{13}$Cl$_2$NO$_2$S$_2$: C, 42.6; H, 3.87; Cl, 20.7%].

EXAMPLE 2

Compound B

A stirred solution of (±)-trans-3-(3-pyridyl)-3-methylthiothiocarbonyl-1,4-oxathiane 4-oxide (560 mg, 1.9 mmol) in ethanol (30 ml) at room temperature was treated with a solution of methylamine (33% in ethanol, 4 ml) and the mixture stirred at room temperature for 30 mins. The mixture was evaporated in vacuo and purified by flash chromatography on silica, eluting with 5% methanol in dichloromethane, to give (±)-trans-N-methyl-3-(3-pyridyl)-1,4-oxathiane-3-carbothioamide 4-oxide (220 mg), m.p. 159°–161° C.;

[Found: C, 48.9; H, 5.29; N, 10.4% Calculated for C$_{11}$H$_{14}$N$_2$O$_2$S$_2$: C, 48.86; H, 5.21; N, 10.36%].

REFERENCE EXAMPLE 1

A stirred solution of 3-(3,4-dichlorophenyl)-1,4-oxathiane 4-oxide (a mixture of cis/trans isomers) (265 mg, 1 mmol) in dimethylformamide (5 ml), under argon, was cooled to −40° C. and treated with potassium tert-butoxide (0.12 g, 1.1 mmol). After 40 mins at this temperature a solution of carbon disulphide (84 mg, 1.1 mmol) in dimethylformamide (0.5 ml) was added and the resulting red solution stirred for a further 1 hour. A solution of methyl iodide (156 mg, 1.1 mmol) in dimethylformamide (0.5 ml) was added and the resulting solution stirred for a further 2 hours. The reaction mixture was then poured into a mixture of dichloromethane (25 ml) and aqueous ammonium chloride solution (25 ml). The organic layer was separated, dried (MgSO$_4$) and evaporated in vacuo to provide an orange oil which was purified by flash chromatography on silica, eluting with 25% ethyl acetate in toluene, to give (±)-trans-3-(3,4-dichlorophenyl)-3-methylthiothiocarbonyl-1,4-oxathiane 4-oxide (0.11 g), as orange crystals m.p. 147°–150° C.

REFERENCE EXAMPLE 2

A stirred solution of 3-(3,4-dichlorophenyl)-1,4-oxathiane (1 g, 4 mmol) in dichloromethane (10 ml) at 0° C. was treated with a solution of meta-chloroperoxybenzoic acid (85%, 860 mg, 4 mmol) in dichloromethane (10 ml) and stirred at 0° C. for 30 mins then at room temperature for 3 hrs. The mixture was shaken with aqueous sodium bicarbonate solution and the organic phase separated, dried (MgSO$_4$) and evaporated to give a solid which was triturated with hexane/toluene (1:1) to give 3-(3,4-dichlorophenyl)-1,4-oxathiane 4-oxide (860 mg), as a colourless crystalline solid, m.p. 100°–103° C.;

[Found: C, 45.5; H, 3.8; Cl, 26.9% Calculated for C$_{10}$H$_{10}$Cl$_2$OS: C, 45.3; H, 3.8; Cl, 26.7%].

REFERENCE EXAMPLE 3

A stirred solution of 3,4-dichlorophenylmagnesium bromide [prepared from 3,4-dichlorobromobenzene (10.2 g, 45 mmol) and magnesium (1.1 g, 45 mmol) in the usual fashion] was treated with a solution of 3-chloro-1,4-oxathiane [prepared from 1,4-oxathiane (2.6 g, 25 mmol) using the method of Tuleen and Bennet *J. Het. Chem.* 1969, 6, 115] in benzene (30 ml), maintaining the temperature of reaction below 10° C. The mixture was allowed to stand at room temperature overnight. It was then poured into ammonium chloride solution (50 ml), the organic phase was separated and the aqueous washed with ether (2×40 ml). The combined organic extracts were dried (MgSO$_4$) and purified by flash chromatography on silica eluting with toluene/hexane (1:1) to give 3-(3,4-dichlorophenyl)-1,4-oxathiane (4.5 g), as colourless crystals, m.p. 65°–68° C.;

[Found: C, 48.6; H, 4.05; Cl, 28.3; S, 12.7% Calculated for C$_{10}$H$_{10}$Cl$_2$OS: C, 48.32; H, 4.05; Cl, 28.5; S, 12.9%].

REFERENCE EXAMPLE 4

A solution of carbon disulphide (216 mg, 2.8 mmol) and 3-(3-pyridyl)-1,4-oxathiane 4-oxide (280 mg, 1.4 mmol) in dimethylformamide (1 ml) was cooled and added to a solution of potassium tert-butoxide (320 mg, 2.8 mmol) in dimethylformamide (20 ml) in a dry ice-/acetone bath at −70° C. After 5 mins a solution of methyl iodide (403 mg, 2.8 mmol) in dimethylformamide (1 ml) was added. After 30 min the mixture was poured into ethanol (50 ml) and evaporated in vacuo. The residue was purified by flash chromatography eluting with 3% methanol in dichloromethane to give (±)-trans-3-(3-pyridyl)-3-methylthiothiocarbonyl-1,4-oxathiane 4-oxide (180 mg), as an orange oil.

REFERENCE EXAMPLE 5

A stirred solution of 2-(3-pyridylmethylsulphinyl)ethanol (0.25 g, 1.35 mmol) in dimethylformamide (25 ml) at 0° C. was treated portionwise with potassium tert-butoxide (0.15 g, 1.35 mmol) and stirred for 10 mins. Formaldehyde gas [generated by heating paraformaldehyde (45 mg, 1.5 mmol) at 150° C.] was passed into the reaction mixture in a rapid stream of argon whilst cooling in an ice bath. When addition of the formaldehyde was completed the cooling bath was removed and the mixture allowed to warm to room temperature over 15 mins. The solution was poured into ethanol (30 ml), neutralised with concentrated hydrochloric acid and filtered to give a clear solution which was evaporated in vacuo and the residue was purified by flash chromatography on silica, eluting with 7% methanol in dichloromethane, to give 3-(3-pyridyl)-1,4-oxathiane 4-oxide (900 mg), as a colourless crystalline solid, m.p. 74°–76° C.

REFERENCE EXAMPLE 6

A stirred solution of 2-(3-pyridylmethylthio)ethanol (3.38 g, 20 mmol) in dichloromethane (50 ml) at 0° C. was treated dropwise with a solution of m-chloroperoxybenzoic acid in dichloromethane (50 ml). The mixture was stirred at 0° C. for 1 hr and at room temperature for 3 hrs. The mixture was evaporated in vacuo and purified by flash chromatography on silica eluting with 20% methanol in ethyl acetate to give 2-(3-pyridylmethylsulphinyl)ethanol (3.5 g), as colourless crystals, m.p. 84°–86° C.;

[Found: C, 51.9; H, 6.14; N, 7.6; S, 17.2% Calculated for $C_8H_{11}NO_2S$: C, 51.85; H, 5.98; N, 7.6; S, 17.3%].

REFERENCE EXAMPLE 7

A stirred solution of sodium ethoxide (4.6 g of sodium in 100 ml ethanol) was treated with 2-mercaptoethanol (7.8 g, 0.1 mol) followed by 3-chloromethylpyridine hydrochloride (16.4 g, 0.1 mol). The mixture was then refluxed under argon for 3.5 hours, filtered and evaporated in vacuo and the residue purified by flash chromatography on silica, eluting with 3% methanol in ethyl acetate, to give 2-(3-pyridylmethylthio)ethanol (13 g), as a yellow oil;

[Found: C, 56.3; H, 6.6; N, 8.2; S, 18.8% Calculated for $C_8H_{14}NOS$: C, 56.8; H, 6.55; N, 8.27; S, 18.9%].

The present invention includes within its scope pharmaceutical compositions which comprise a compound of general formula (I) or a pharmaceutically acceptable salt thereof, in association with a pharmaceutically acceptable carrier or coating. In clinical practice the compounds of the present invention may be administered rectally, but are preferably administered parenterally, by inhalation if appropriate, or, more preferably, orally.

Solid compositions for oral administration include compressed tablets, pills, powders and granules. In such solid compositions, one or more of the active compounds is, or are, admixed with at least one inert diluent such as starch, sucrose or lactose.

The compositions may also comprise, as is normal practice, additional substances other than inert diluents, e.g. lubricating agents, such as magnesium stearate.

Liquid compositions for oral administration include pharmaceutically acceptable emulsions, inert diluents commonly used in the art such as water and liquid paraffin. Besides inert diluents such compositions may comprise adjuvants, such as wetting, and suspending agents, and sweetening, flavouring, perfuming and preserving agents. The compositions according to the invention for oral administration also include capsules of absorbable material such as gelatin, containing one or more of the active substances with or without the addition of diluents or excipients.

Compositions according to the invention for parenteral administration include sterile aqueous, aqueous-organic, and organic solutions, suspensions and emulsions. Examples of organic solvents or suspending media are propylene glycol, polyethylene glycol, vegetable oils such as olive and injectable organic esters such as ethyl oleate. The compositions may also contain adjuvants such as stabilising, preserving, wetting, emulsifying and dispersing agents. They may be sterilised by, for example, filtration through a bacteria-retaining filter, by incorporation in the compositions of sterilizing agents, by irradiation or by heating. They may also be manufactured in the form of sterile solid compositions, which can be dissolved in sterile water or some other sterile injectable medium immediately before use.

Compositions for inhalation may be sterile aqueous solutions which are then nebulised or dry powders formulated in accordance with known methods.

Solid compositions for rectal administration include suppositories formulated in accordance with known methods and containing one or more of the compounds of formula (I) or a pharmaceutically acceptable salt thereof.

The percentage of active ingredient in the composition of the invention may be varied, it being necessary that it should constitute a proportion such that a suitable dosage shall be obtained. Obviously, several unit dosage forms may be administered at about the same time. The dose employed will be determined by the physician, and depends upon the desired therapeutic effect, the route of administration, the duration of the treatment and the condition of the patient. In the adult, the doses are generally from about 0.001 to about 50, preferably from about 0.01 to about 5, mg/kg body weight per day by oral administration. By inhalation, either as a nebulised solution or as a formulated dry powder, the preferred daily dosage is from about 0.001 to about 5, preferably from about 0.01 to about 0.5, mg/kg body weight.

The compounds may also be applied topically for inhibition of head hair loss associated with male pattern baldness, the preferred daily dosage being from 0.1 to 10 mg/kg body weight applied, for example, in 5 ml portions two or three times per day.

The following Example illustrates pharmaceutical compositions according to the present invention.

COMPOSITION EXAMPLE

No. 2 size gelatin capsules each containing:

| | |
|---|---|
| (±)-trans-3-(3,4-dichlorophenyl)-N-methyl-1,4-oxathiane-3-carbothioamide 4-oxide | 20 mg |
| lactose | 100 mg |
| starch | 60 mg |
| dextrin | 40 mg |
| magnesium stearate | 1 mg | were prepared in accordance with the usual procedure.

We claim:

1. A compound of the formula

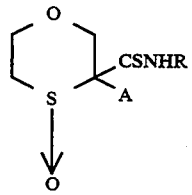

where R is lower alkyl and A is pyridyl unsubstituted or substituted by lower alkyl, lower alkoxy or halo; or a pharmaceutically acceptable salt thereof.

2. A compound according to claim 1 where the —CSNHR group is trans to the oxygen atom attached to sulfur.

3. A compound according to claim 1 where R is methyl.

4. A compound according to claim 1 where A is pyrid-3-yl.

5. A compound according to claim 4 which is (+)-trans-N-methyl-3-(3-pyridyl)-1,4-oxathian-3-carbothioamide-4-oxide, or a pharmaceutically acceptable salt thereof.

6. A pharmaceutical composition for use in the treatment or prophylaxis of a disorder in need of vaso-relaxant activity which composition comprises a therapeutically effective amount of a compound of claim 1 in an amount effective to relax vascular smooth muscle in association with a pharmaceutically acceptable carrier or diluent.

* * * * *